United States Patent [19]

Withers, Jr. et al.

[11] Patent Number: 4,634,800

[45] Date of Patent: Jan. 6, 1987

[54] METHANE CONVERSION PROCESS

[75] Inventors: Howard P. Withers, Jr., Douglassville; C. Andrew Jones, Newtown Square; John J. Leonard, Springfield; John A. Sofranko, Malvern, all of Pa.

[73] Assignee: Atlantic Richfield Company, Los Angeles, Calif.

[21] Appl. No.: 738,115

[22] Filed: May 24, 1985

Related U.S. Application Data

[63] Continuation-in-part of Ser. No. 600,656, Apr. 16, 1984, Pat. No. 4,523,049, and Ser. No. 600,670, Apr. 16, 1984, Pat. No. 4,523,050.

[51] Int. Cl.$^4$ .................................................. C07C 2/00
[52] U.S. Cl. ............................... 585/500; 585/415; 585/417; 585/418; 585/654; 585/656; 585/658; 585/661; 585/700; 585/943
[58] Field of Search ............... 585/500, 943, 654, 656, 585/658, 661, 415, 417, 418, 700

[56] References Cited

U.S. PATENT DOCUMENTS

| | | | |
|---|---|---|---|
| 4,199,533 | 4/1980 | Benson | 585/500 |
| 4,450,310 | 5/1984 | Fox et al. | 585/943 |
| 4,467,130 | 8/1984 | Olah | 585/943 |
| 4,523,049 | 6/1985 | Jones et al. | 585/500 |

OTHER PUBLICATIONS

Hinsen and Baerns, "Oxidative Koppling via Methan zu $C_2$-Kohlenwasserstoffen in Gegenwart unterschiedlicher Katalysatoren", Chemical Zeitung, vol. 107 (1983) pp. 223-226.
Keller and Bhasen, Synthesis of Ethylene Via Oxidative Coupling of Methane, J. of Catalysis 73, 9-19 (1982).

Primary Examiner—William R. Dixon, Jr.
Assistant Examiner—Cynthia A. Prezlock
Attorney, Agent, or Firm—Craig E. Larson

[57] ABSTRACT

An improved method for converting methane to higher hydrocarbon products by contacting a hydrocarbon gas comprising methane, an oxygen-containing gas and a reducible metal oxide under conditions effective to produce higher hydrocarbon products and water, the improvement which comprises conducting the contacting in the presence of at least one promoter selected from the group consisting of halogens and compounds thereof.

23 Claims, No Drawings

METHANE CONVERSION PROCESS

CROSS REFERENCE TO RELATED APPLICATION

This application is a continuation-in-part of U.S. patent application Ser. Nos. 600,656 now Pat. No. 4,523,049 and 600,670, now Pat. No. 4,523,050 both filed April 16, 1984. The entire content of each of these applications incorporated by reference.

BACKGROUND OF THE INVENTION

This invention relates to the synthesis of hydrocarbons from a methane source. A particular application of this invention is a method for converting natural gas to more readily transportable material.

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons carbons although some ethane may be included. Gas conditioning is required to alter the composition of wellhead gas, processing facilities usually being located in or near the production fields. Conventional processing of wellhead natural gas yields processed natural gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion of olefins such as ethylene or propylene would be extremely valuable to the chemical industry.

Recently, it has been discovered that methane may be converted to higher hydrocarbons (e.g., ethane, ethylene and higher homologs) by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regenerating a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See U.S. Pat. Nos. 4,443,649; 4,444,984; 4,443,648; 4,443,645; 4,443,647; 4,443,644; and 4,443,646.

U.S. Pat. No. 4,554,395, discloses and claims a process which comprises contacting methane with an oxidative synthesizing agent under elevated pressure (e.g., 2–100 atmospheres) to produce greater amounts of $C_3+$ hydrocarbon products.

U.S. Pat. No. 456,082, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

U.S. Pat. No. 4,499,322 discloses and claims a process for the conversion of methane to higher hydrocarbons which comprises contacting methane with an oxidative synthesizing agent containing a promoting amount of alkali metal and/or compounds thereof.

U.S. Pat. No. 4,495,374 discloses and claims a process for the conversion of methane to higher hydrocarbons which comprises contacting methane with an oxidative synthesizing agent containing a promoting amount of alkaline earth metal and/or compounds thereof.

U.S. Pat. No. 4,499,323 discloses and claims a process for the conversion of methane to higher hydrocarbons which comprises contacting methane with a contact solid comprising a reducible oxide of praseodymium and at least one member of the group consisting of alkali metals, and compounds thereof.

Commonly-assigned U.S. patent application Ser. No. 06/600,918 discloses and claims a process for the conversion of methane to higher hydrocarbons which comprises contacting methane with a contact solid comprising a reducible oxide of terbium and at least one member of the group consisting of alkali metals, alkaline earth metals, and compounds thereof. The entire content of this application is incorporated herein by reference.

U.S. Pat. No. 4,499,324 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof.

Commonly-assigned U.S. patent application Ser. No. 06/600,730 discloses and claims a process for the conversion of methane to higher hydrocarbons which comprises contacting methane with a contact solid comprising a reducible oxide of iron and at least one member of the group consisting of alkali metals, alkaline earth metals, and compounds thereof. The entire content of this application is incorporated herein by reference.

U.S. Pat. No. 4,489,215 discloses and claims a process for the conversion of methane to higher hydrocarbons which comprises contacting methane with a contact solid comprising a reducible oxide of ruthenium and at least one member of the group consisting of alkali metals, alkaline earth metals, and compounds thereof. The entire content of this patent is incorporated herein by reference.

In a typical application of the foregoing processes for the oxidative conversion of methane, methane feed is contacted with a reducible metal oxide and regeneration is accomplished separately by contacting the reduced metal oxide with an oxygen-containing gas (e.g., air). Thus, a cyclic redox process results in which methane reaction and reoxidation of the metal oxide "reagent" are performed separately and repeatedly for a continuous process.

Such a procedure presents several disadvantages for large scale continuous operation. One disadvantage is the large quantity of solid cycling between methane reaction and reoxidation in such a way that the methane and oxygen are not mixed. Another disadvantage is the necessity of developing a composition that is resistant to mechanical attrition and repeated exposure to reductive and oxidative environments.

U.S. patent application No. 4,547,610 discloses and claims a process for the conversion of methane to higher hydrocarbons by contacting methane with reducible metal oxides in the presence of oxides of nitrogen. The entire content of this application is incorporated herein by reference.

Hinsen and Baerns report studies of a continuous mode for the oxidative coupling of methane wherein regenerating air is cofed with the methane feed. Hinsen, W. and Bearns, M., "Oxidative Kopplung von Methan zu C$_2$-Kohlenwasserstoffen in Gegenwart unterschiedlicher Katalysatoren", Chemiker-Zeitung, Vol. 107, No. 718, pp. 223-226 (1983). Using a catalyst based on lead oxide and gamma-alumina in a fixed bed reactor operated at 1 atmosphere total pressure and 600°-750° C., they report results of approximately 53% selectivity to ethane and ethylene at 8% methane conversion for a feed consisting of about 50% methane, 25% air and 25% nitrogen. Other metal oxides studied by Hinsen and Baerns included oxides of Bi, Sb, Sn and Mn.

U.S. Pat. No. 4,523,049, discloses and claims a process for the converting of methane to higher hydrocarbons which comprises contacting methane and an oxygen-containing gas with a solid comprising a reducible metal oxide and an alkali/alkaline earth metal promoter. The entire content of this application is incorporated herein by reference.

U.S. Pat. No. 4,523,050 discloses and claims a process for the converting of methane to higher hydrocarbons which comprises contacting methane and an oxygen-containing gas with a manganese silicate. The entire content of this application is incorporated herein by reference.

SUMMARY OF THE INVENTION

It has now been found that the conversion of methane to higher hydrocarbons by contacting a gas comprising methane and a gaseous oxidant with a reducible metal oxide may be improved by conducting the contacting in the presence of at least one promoter selected from the group consisting of halogens and compounds thereof. The promoter may be incorporated into solids comprising reducible metal oxides prior to conducting the contacting, or the promoter may be at least periodically introduced with methane- and oxygen-containing gases while conducting the contacting. The contact solid comprises at least one reducible oxide of at least one metal which oxide(s) when contacted with methane at methane conversion conditions (preferably at a temperature within the range of about 500° to 1000° C.) are reduced and produce higher hydrocarbon products and water. Preferably, the contact solid further comprises at least one promoter selected from the group consisting of alkali metals, alkaline earth metals, and compounds thereof.

Halogens are selected from the group consisting of fluorine, chlorine, bromine and iodine. Preferred halogen promoters are chlorine, bromine and compounds thereof. Chlorine and compounds of chlorine are particularly preferred.

Reducible oxides include oxides of metals selected from the group consisting of Mn, Sn, In, Ge, Pb, Sb and Bi. Reducible oxides also include oxides of metals selected from the group consisting of Pr, Tb, Ce, Fe and Ru. Reducible oxides of Mn are preferred.

Alkali metals are selected from the group consisting of Li, Na, K, Rb, and Cs. Alkaline earth metals are selected from the group consisting of Mg, Ca, Sr and Ba. Mg and Ca are preferred alkaline earth promoters. However, alkali metal promoters are more preferred promoters. Of the alkali metals, lithium and sodium are preferred. Sodium is particularly preferred.

The improved process of the present invention produces higher methane conversion at similar hydrocarbon selectivity or increased hydrocarbon selectivity at similar methane conversion, as compared to prior methods.

DETAILED DESCRIPTION OF THE INVENTION

In addition to methane the hydrocarbon feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The gaseous oxidant is selected from the group consisting of molecular oxygen, oxides of nitrogen, and mixtures thereof. Preferably, the gaseous oxidant is an oxygen-containing gas. A preferred oxygen-containing gas is air. Suitable oxides of nitrogen include $N_2O$, $NO$, $N_2O_3$, $N_2O_5$ and $NO_2$. Nitrous oxide ($N_2O$) is a presently preferred oxide of nitrogen.

The ratio of hydrocarbon feedstock to gaseous oxidant gas is not narrowly critical to the present invention. However, the ratio will desirably be controlled to avoid the formation of gaseous mixtures within the flammable region. The volume ratio of hydrocarbon/gaseous oxidant is preferably within the range of about 0.1-100:1, more preferably within the range of about 1-50:1. Methane gaseous oxidant feed mixtures containing about 50 to 90 volume % methane have been found to comprise a desirable feedstream.

The contact solid which is contacted with methane in the first stage of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and y designate the relative atomic proportions of metal and oxide in the composition) and/or (2) one or more oxygen-containing metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof.

Reducible oxides of cerium, praseodymium, and terbium have also been found to be effective for the conversion of methane to higher hydrocarbons, particularly when the rare earth component is associated with an alkali metal component and/or an alkaline earth metal component. Reducible oxides of iron and ruthenium are also effective, particularly when associated with an alkali or alkaline earth component.

Halogen promoters are preferably introduced into the process with gaseous feedstreams flowing tdo the process. Any suitable concentration of promoter can be used (e.g., about 0.01-99 vol. % promoter based on total gaseous feedstream). The promoter can be introduced continuously or periodically, although continuous introduction is preferred. Suitable sources of halogen include free halogen gas, hydrogen halides, ammonium halides, aliphatic halides (e.g., methyl halide, methylene halide, ethyl halide, amyl halide, allyl halide), cycloaliphatic halides (e.g., cyclohexyl halide), halogen substituted aliphatic acids such as methyl amine hydrochloride, and the like. Mixtures of various halogen sources may be used. Higher concentrations of halogen promoter lead to the formation of halogenated hydrocarbons. Presently preferred are free halogen gas, aliphatic halides and hydrogen halides. Methane/gaseous oxidant feed mixtures containing about 0.01 to 10 vol. % halogen promoter, preferably about 0.1 to 5 vol. %, are desirable feedstreams.

The contact solid employed in the process of the present invention may contain, in addition to the reducible metal oxide component, at least one halogen component. The atomic ratio in which these materials are combined to form the contact solid is not narrowly critical. However, the preferred atomic ratio of the reducible oxide component (expressed as the metal, e.g., Mn) to the halogen component (expressed as the halogen, e.g., Cl) may range up to about 1.5, more preferably the ratio is within the range of about 1.3 to 1000:1.

The contact solid employed in the process of the present invention may contain, in addition to the reducible metal oxide component, at least one alkali or alkaline earth metal. The atomic ratio in which these materials are combined to form the contact solid is not narrowly critical. However, the preferred atomic ratio of the reducible oxide component (expressed as the metal, e.g., Mn) to the alkali/alkaline earth metal component (expressed as the metal, e.g., Na) is within the range of about 0.1-100:1, more preferably within the range of about 0.3-10:1.

The contact solid may optionally contain at least one phosphorus component. The amount of phosphorus contained in the contact solid is again not narrowly critical. The atomic ratio of phosphorus to the reducible oxide component (expressed as the metal, e.g., Mn) is preferably less than about 2:1. More preferably, this ratio is within the range of about 0.1-0.5:1.

A preferred contact solid used in the process of this invention may be further expressed by the following empirical formula:

$$A_a B_b C_c P_d O_e$$

wherein A is selected from the group consisting of Mn, Sn, In, Ge, Pb, Sb, Bi, Pr, Tb, Ce, Fe, Ru and mixtures thereof; B is selected from the group consisting of F, Cl, Br, I, and mixtures thereof; C is selected from the group consisting of alkali and alkaline earth metals and mixtures thereof; a to e indicate the atomic ratio of each component; and when a is 10, b is within the range of about 0.01-30, c is within the range of about 0-33, d is within the range of about 0-20, and e has a value which is determined by the valence and proportions of the other elements present.

The metal components may be associated with support materials such as silica, alumina, titania, magnesia, zirconia and the like and combinations thereof. When employing agents containing rare earth components—oxides of Ce, Pr, and Tb—the rare earth oxides preferably serve as supports. Similarly, when employing oxides of Fe and Ru, those oxides preferably serve as supports.

Reducible oxides of manganese have been found to be particularly desirable for methane conversion according to the method of the present invention when associated with an alkali metal (preferably sodium). Particularly preferred agents comprise silica- and/or magnesia-supported solids containing oxides of manganese and sodium.

The solid can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the agent, it is desirable to provide it in the form of a phosphate of an alkaline metal or alkaline earth metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined, preferably in air, at a temperature within the range of about 300° to 1200° C. Particular calcination temperatures will vary depending upon the particular metal compound or compounds employed.

Halogen components may conveniently be incorporated into the contact solid either before or after calcination of the metal-containing composite. A suitable method of incorporation is to impregnate the composite with solutions containing the desired halogens. Suitable compounds for impregnation include $NH_4Cl$, NaCl, HCl and $MCl_x$. Another suitable method of incorporation is to contact the composite with a halogen source.

The halogen source may be any of a wide number of materials. The source may be either free halogen gas or a compound of halogen. Suitable sources of halogen include hydrogen iodide, hydrogen bromide, and hydrogen chloride; ammonium halides; aliphatic halides such as methyl chloride, methylene chloride, ethyl chloride, amyl chloride and allyl chloride, cycloaliphatic halides such as cyclohexyl halide; halogen substituted aliphatic acids such as methyl amine hydrochloride, and the like. Mixtures of various halogen sources may be used. The presently preferred halogen sources are free halogen gas, aliphatic halides and hydrogen halides.

Regardless of how the components of the agent are combined, the composite will be dried and calcined at elevated temperatures prior to use of the process of this invention.

Preferably, methane and oxygen are contacted with the agent in the substantial absence of catalytically effective nickel, noble metals and compounds thereof. (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the method of this invention relative to such contacting in the absence of such metals and compounds thereof.

Operating temperatures for the method of this invention are generally within the range of about 300° to 1200° C., more preferably within the range of about 500° to 1000° C. Best results for contact solids containing manganese have been found at operating temperatures within the range of about 800° to 900° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressures of methane and oxygen have been found to effect overall results. Preferred operating pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 10 to 100,000 hr.$^{+1}$, more preferably within the range of about 600 to 40,000 hr.$^{-1}$.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in the method of the present invention occurs "in situ"—by contact of the reduced metal oxide with the gaseous oxidant cofed with methane to the contact zone.

The contact solids may be maintained in the contact zone as fixed, moving, or fluidized beds of solids. A fixed bed of solids is currently preferred for the method of this invention.

When halogen-promoted contact solids are employed in the methane conversion process of this invention, it has been found that the enhanced methane conversion activity and selectivity to higher hydrocarbons attributable to the halogen component is dissipated over time. Therefore, additional halogen component must be incorporated into the contact solid in order to maintain the desirable results obtained by this invention. Preferably, a halogen source is at least periodically introduced with methane- and oxygen-containing gases during the contacting step.

The effluent from the contact zone contains higher hydrocarbon products (e.g., ethylene, ethane and other light hydrocarbons), carbon oxides, water, unreacted hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

The invention is further illustrated by reference to the following examples. Experimental results reported below include conversions and selectivities calculated on a carbon mole basis.

EXAMPLE 1

A contact solid consisting of 15 wt. % Mn/5 wt. % $Na_4P_2O_7$ on silica was prepared by impregnating the silica support with appropriate amounts of sodium pyrophoshate and manganese (as manganese acetate). The impregnated solid was dried for 2 hours at 110° C. and then calcined in air for 16 hours at 850° C. A quartz tube reactor (12 mm. inside diameter) was charged with 10 ml. of the calcined solids and the reactor was heated to reaction temperature with a stream of heated nitrogen. Results obtained when methane/air/HCl mixtures were contacted with the solid are shown below in Table 1. Also shown for comparison are corresponding results obtained in the absence of the HCl promoter. All runs were performed at a $CH_4$ GHSV of 3600 hr.$^{-1}$.

TABLE I

| Temp. (°C.) | Vol. % in Feed | | % Conv. | | % Selectivity to: | | | | | | |
|---|---|---|---|---|---|---|---|---|---|---|---|
| | Air | HCl | $CH_4$ | $O_2$ | $C_2=$ | $C_2$ | $C_3=$ | $>C_4$ | CO | $CO_2$ | $C_2+$ |
| 775 | 20 | 0 | 5 | | | | | | | | 58 |
| 775 | 20 | 0.5 | 13 | | | | | | | | 91 |
| 775 | 50 | 0 | 11 | 33 | 11 | 22 | 4 | 0 | 18 | 48 | 34 |
| 775 | 50 | 0.5 | 26 | 92 | 48 | 13 | 6 | 5 | 17 | 11 | 72 |
| 825 | 50 | 0 | 15 | 62 | 23 | 28 | 2 | trace | 13 | 23 | 53 |
| 825 | 50 | 0.5 | 26 | 93 | 46 | 11 | 5 | 5 | 19 | 14 | 67 |
| 900 | 50 | 0 | 21 | 91 | 39 | 20 | 4 | 2 | 16 | 18 | 65 |
| 900 | 50 | 0.5 | 24 | 93 | 53 | 9 | 5 | 5 | 18 | 9 | 72 |

EXAMPLE 2

The example was carried out in the same manner as Example 1 except that the solid employed was 12.5 wt. % $NaMnO_2$ on magnesia. The solid was prepared by impregnating magnesia with the appropriate amount of sodium permanganate and drying and calcining the solid. All runs shown below in Table II were performed at a CH$_4$ GHSV of 3600 hr.$^{-1}$.

TABLE II

| Temp. (°C.) | Vol. % in Feed | | % Conv. | | % Selectivity to: | | | | | | |
|---|---|---|---|---|---|---|---|---|---|---|---|
| | Air | HCl | CH$_4$ | O$_2$ | C$_2$= | C$_2$ | C$_3$= | >C$_4$ | CO | CO$_2$ | C$_2$+ |
| 775 | 50 | 0 | 4 | 15 | 12 | 51 | 1 | 0 | 5 | 31 | 64 |
| 775 | 50 | 0.5 | 16 | 27 | 40 | 31 | 6 | 2 | 4 | 16 | 79 |
| 825 | 50 | 0 | 22 | 92 | 34 | 31 | 5 | 1 | 1 | 28 | 71 |
| 825 | 50 | 0.5 | 28 | 93 | 54 | 13 | 7 | 5 | 9 | 11 | 79 |

What is claimed is:

1. In an improved method for converting methane to higher hydrocarbon products and coproduct water wherein a gas comprising methane and a gaseous oxidant are contacted with a solid comprising at least one reducible oxide of at least one metal which oxide when contacted with methane at a temperature within the range of about 500 to 1000° C. is reduced and produces higher hydrocarbon products and water, the improvement which comprises conducting the contacting in the presence of at least one promoter selected from the group consisting of halogens and compounds thereof.

2. The method of claim 1 wherein the gaseous oxidant comprises molecular oxygen.

3. The method of claim 1 wherein the gaseous oxidant comprises oxides of nitrogen.

4. The method of claim 3 wherein the oxides of nitrogen comprise N$_2$O.

5. The method of claim 1 wherein methane and the gaseous oxidant are contacted with said solid at a temperature within the range of about 300 to 1200° C.

6. The method of claim 1 wherein methane and the gaseous oxidant are contacted with said solid at a temperature within the range of about 500° to 1000° C.

7. The method of claim 1 wherein said solid comprises a reducible oxide of Mn.

8. The method of claim 7 wherein the gaseous oxidant is an oxygen-containing gas.

9. The method of claim 8 wherein methane and the oxygen-containing gas are contacted with said solid at a temperature within the range of about 800° to 900° C.

10. The method of claim 1 wherein a halogen source is at least periodically introduced with methane and the gaseous oxidant to contact the solid.

11. The method of claim 1 wherein the promoter is selected from the group consisting of F, Cl, Br, I and compounds thereof.

12. The method of claim 1 wherein the promoter is chlorine or compounds thereof.

13. The method of claim 1 wherein the promoter is bromine or compounds thereof.

14. The method of claim 1 wherein said solid further comprises at least one member of the group consisting of alkali metals, alkaline earth metals and compounds thereof.

15. The method of claim 1 wherein said solid further comprises at least one member of the group consisting of alkali metals and compounds thereof.

16. The method of claim 1 wherein said solid further comprises at least one member of the group consisting of sodium and compounds thereof.

17. The method of claim 1 wherein said solid further comprises at least one member of the group consisting of lithium and compounds thereof.

18. The method of claim 1 wherein said solid further comprises at least one member of the group consisting of alkaline earth metals and compounds thereof.

19. The method of claim 1 wherein said solid further comprises at least one member of the group consisting of magnesium and compounds thereof.

20. The method of claim 1 wherein said solid further comprises at least one member of the group consisting of calcium and compounds thereof.

21. The method of claim 1 wherein said solid further comprises at least one reducible oxide of at least one metal selected from the group consisting of Mn, Sn, In, Ge, Pb, Sb and Bi.

22. The method of claim 14 wherein the solid comprises at least one reducible oxide of at least one metal selected from the group consisting of Pr, Tb and Ce.

23. The method of claim 14 wherein the solid comprises at least one reducible oxide of at least one metal selected from the group consisting of Fe and Ru.

* * * * *